United States Patent [19]

Hardwick

[11] Patent Number: 4,469,100

[45] Date of Patent: Sep. 4, 1984

[54] INTUSSUSCEPTING BALLOON CATHETER FOR STONE EXTRACTION

[76] Inventor: Charles W. Hardwick, 112 Crystal View South, Sanford, Fla. 32771

[21] Appl. No.: 474,796

[22] Filed: Mar. 14, 1983

[51] Int. Cl.³ ............................................. A61B 17/00
[52] U.S. Cl. ..................................... 128/328; 604/96
[58] Field of Search ................. 128/328, 303; 604/93, 604/96-99, 104

[56] References Cited

U.S. PATENT DOCUMENTS

| | | | |
|---|---|---|---|
| 3,074,408 | 1/1963 | Chester | 128/328 |
| 3,827,437 | 8/1974 | Inaba | 128/328 |
| 3,970,090 | 7/1976 | Loiacono | 604/104 |
| 3,972,331 | 8/1976 | Bolduc et al. | 604/97 |
| 4,243,040 | 1/1981 | Beecher | 128/328 |
| 4,324,262 | 4/1982 | Hall | 128/328 |
| 4,430,076 | 2/1984 | Harris | 604/96 |

Primary Examiner—C. Fred Rosenbaum
Assistant Examiner—C. W. Shedd
Attorney, Agent, or Firm—Duckworth, Allen, Dyer & Pettis

[57] ABSTRACT

An extraction device for removing foreign bodies such as a uretal stone from a human body passage. A double lumen catheter is provided having a tubular balloon attached circumjacent to the distal end thereof. A suction lumen is open at the distal end and a pressure applying lumen is open to the interior of the balloon. The balloon includes a lower reentrant portion. After insertion of the distal end of the catheter into the body passage such as the ureter to the point of a stone, the balloon is inflated dilating the ureter. The catheter is slowly withdrawn causing intussusception of the distal end of the tubular balloon, thereby surrounding and captivating the stone. Continued withdrawal extracts the stone without trauma to the passage wall.

13 Claims, 8 Drawing Figures

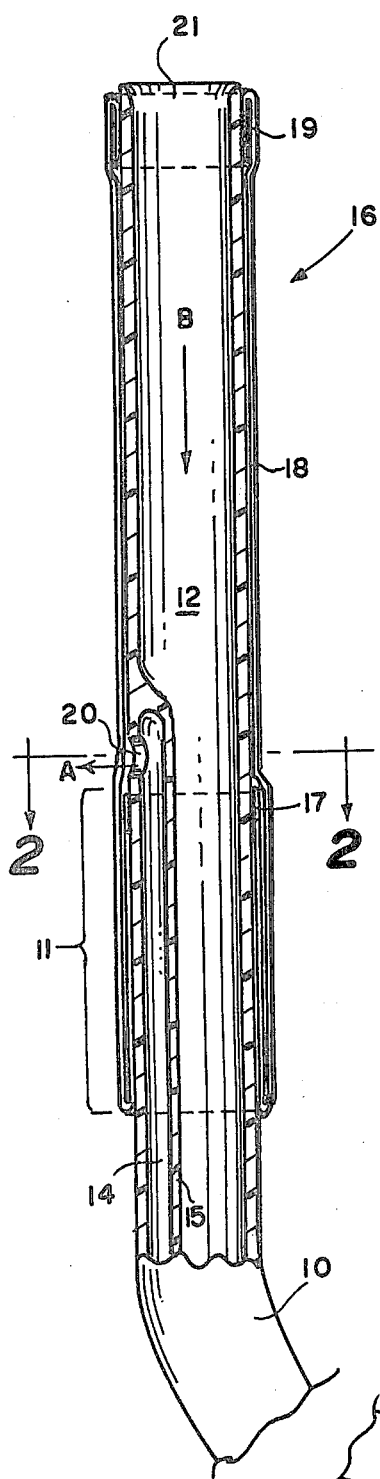
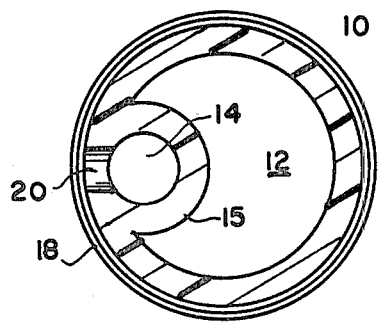
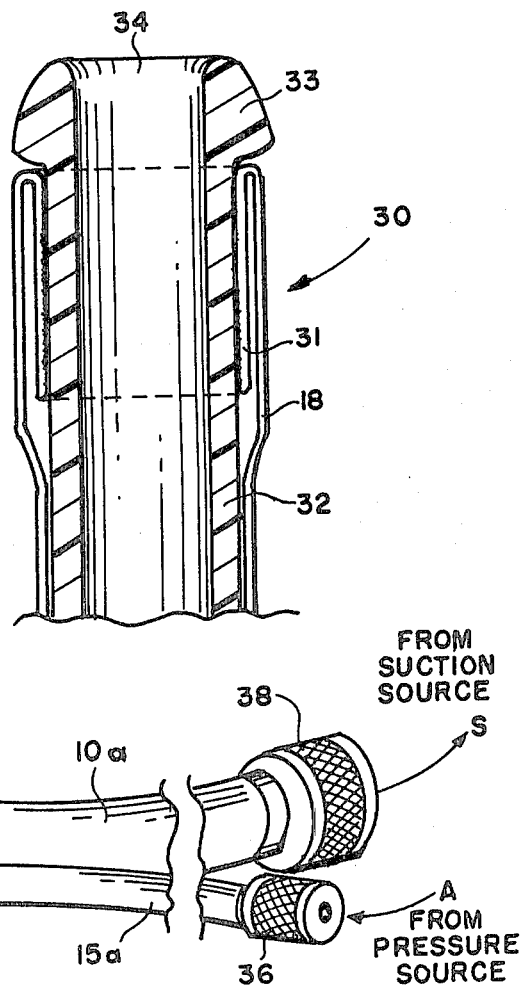

INTUSSUSCEPTING BALLOON CATHETER FOR STONE EXTRACTION

BACKGROUND OF THE INVENTION

1. Field of Invention

The present invention relates to a device for removing objects from passages and the human body, in more particularily to an extracting device for removing kidney stones from the urinary tract.

2. Description of the Prior Art

The formation of stones in the kidneys has been a very serious problem for many years. Such stones, which are formed from calcium or other particulate matter, generally are hard in the form of irregular masses. It is common for these stones to attempt to pass through the ureter, to the urinary bladder. In addition to being extremely painful to the patient, the stones may cause blockage of the urine producing ureteral colic. In some instances, stones will pass normally by the peristalic waves of muscle contracture into the bladder. On the other hand, this action may force an irregular sharp stone into the lining of the ureter, causing swelling or edema which in effect reduces the size of the ureteral lumen.

Stones having a diameter of more than 0.5 centimeter and irregular stones may not pass spontaneously and generally require surgical intervention or extraction.

The most narrow portion of the ureter is the first inch beyond the kidney pelvis and the last inch near the urinary bladder, called the uretero vesical junction. These two locations are the most likely points which will prevent spontaneous passage of a stone. It has been known in the prior art to extract a stone from the uretero vesical junction by means of a "stone basket". These wire basket devices are passed through a cystoscope and into the ureter where they are guided up beyond the stone, if possible. The physician attempts to capture the stone in the wire basket and extract it. However, it is not always possible to pass the device beyond the stone, and the stone may be pushed back into the renal pelvis and lost. Additionally, there is a significant danger of injuring the ureter or even perforation thereof. Also, the stone basket can scrape and injure the ureter from the wires of the basket and from the irregularly shaped stone.

Extractors have been proposed in the prior art which attempt to overcome the disadvantage of the wire basket extractor by the use of catheters having balloons attached to the distal end thereof. For example, one prior art device utilizes a single catheter with two inflatable balloons concentric with the catheter near the distal tip. The catheter is adjusted so that an arrested stone is between the balloons, the balloons inflated and the catheter slowly withdrawn such that the lower balloon dilates the ureter and the upper balloon pushes the stone toward the bladder. However, the stone must be relatively small since it is required to be caught between the catheter and the ureter wall.

An improvement to the two balloon catheter has been provided by Shiahata in U.S. Pat. No. 4,295,464. Here, a double catheter is provided having a balloon at the distal end of each and which provides relatively movement between the two balloons. Although an improvement, the size of the stone which can be captured is limited by the catheter size and the mechanical design of the catheter is relatively complex. A single balloon catheter having a double lumen is taught by Beecher in U.S. Pat. No. 424,243,040. Beecher teaches the use of concentric catheters with the inner catheter movable within the outer catheter. An inflatable balloon is attached at the distal end of the outer catheter and at the distal end of the inner catheter such that the balloon may be inflated by pressure in the lumen formed between the inner and outer catheter. The lumen of the inner catheter provides a clear passage to which a vacuum pump may be connected to produce suction which will permit pulling the stone into the balloon when inflated. The requirement for producing relative motion between the inner and outer catheters requires careful handling on the part of the physician and also results in the device being is relatively complex and expensive to manufacture.

Thus, there is a need for a catheter capable of extracting stones from the ureter which can be manufactured at low cost and therefore be disposable after use, and which will capture a stone in such a manner that no damage can occur to the ureteral walls.

SUMMARY OF MY INVENTION

My invention is a single balloon catheter having a double lumen which overcomes the disadvantages of the prior art balloon catheters for extraction of kidney stones and the like. The catheter may be manufactured having an outside diameter of two to three millimeters (mm). The catheter includes a large lumen open at the distal end and a second smaller lumen integral with the large lumen and closed at the distal end. An orifice from the small lumen is provided a short distance from the distal end through the outer wall of the catheter. A thin wall, inflatable tubular sleeve is attached circumjacent to the distal end of the catheter at one end with the opposite end folded up and attached circumjacently just below the orifice to form a tubular balloon. In its uninflated state, the tubular balloon forms a relatively snug fit around the catheter. The catheter is of appropriate length to permit the catheter to be inserted through a cystoscope into the ureter to a position at the upper end thereof. At the proximal end of the catheter, the catheter is split into two tubes, one connecting to the large lumen and the other connecting to the small lumen.

As will be understood, injection of air, water or other liquid into the small lumen will inflate the elastic balloon via the orifice The large lumen may be connected to a vacuum when suction is required at the distal end of the catheter.

A typical application of my catheter is the extraction of a kidney stone from the ureter. In such application the catheter is inserted into the ureter utilizing a standard cystoscope and inserted until stone is contacted. At that point, the balloon may be inflated with air, water or a contrast medium, sufficient pressure is applied to the balloon to dilate the ureter to a diameter larger than the stone. As pressure is maintained in the balloon, suction may be applied to the open lumen which will tend to draw the stone against the tip of the catheter. Since the ureter is now dilated to a diameter somewhat greater than the size of the stone, withdrawal of the catheter will generally permit the stone to drop in reponse to the urine pressure above the stone and the suction from the catheter. Due to the pressure of the balloon against the ureter wall and the thinness of the balloon material, the balloon will intussuscept. As the intussusception occurs; the balloon tends to surround the stone. As the catheter continues to be withdrawn total intussusception will occur and the balloon will have captured the stone. Maintaining the pressure of the balloon to dilate the ureter while slowly withdrawing the catheter will cause the balloon and stone to be pulled downward and eventually into the bladder. The combination of the captivation of the stone by the intussuscepted balloon and the suction applied by the catheter permits the extraction of the stone. The provision of double layered balloon walls between the stone and the ureter wall prevents trauma or damage thereto which could otherwise occur with prior extractors. In some instances, the inflation of the tubular balloon distends the uretal wall sufficiently to permit movement of the stone downward through the ureter without the necessity for captivation by the intussuscepting portion of the balloon.

The balloon catheter of my invention can be produced at relatively low cost due to its simple construction and the lack of moving parts permits ease of handling during a stone extraction procedure. The unit may be provided in a sterilized package as a disposable device.

It is therefore a principal object of my invention to provide a balloon catheter having an intussuscepting balloon for dilating the ureter to permit moving of a stone for withdrawal down the ureter.

It is another object of my invention to provide a balloon catheter having an intussuscepting balloon for dilating the ureter and capturing a stone for withdrawal.

It is another object of my invention to provide a stone extracting balloon catheter which envelops a stone to be removed by the balloon to prevent damage to the ureteral walls.

It is still another object of my invention to provide a double lumen integral catheter having an open lumen for supplying vacuum to a captured stone and a second closed lumen having an aperature into the interior of the balloon to permit inflation of the balloon.

It is yet another object of my invention to provide a balloon catheter which may inserted into the ureter or other bodily passage, inflated to dilate the passage and withdrawn to cause intussusception of the distal end of the balloon.

It is a further object of the invention to provide a double lumen catheter in which connections are provided at the proximal end to the suction lumen and to the inflation lumen.

It is still a further object of my invention to provide a balloon catheter for extraction of stones and the like which may be produced at low cost and disposed of after a single use.

These and other objects and advantages of my invention will become apparant from the following description and drawings.

BRIEF DESCRIPTION OF THE DRAWINGS

FIG. 1 is a view of the catheter of my invention showing cross sectional view of the distal end thereof with the balloon portion in its uninflated condition;

FIG. 2 is a cross section of the distal end of my catheter through section 2—2 of FIG. 1;

FIG. 3 is a cross sectional view of the distal end of an alternative embodiment of the catheter of FIG. 1;

FIGS. 4 through 8 show various stages in a typical application of the invention by means of a cross sectional view through a stone-containing ureter with;

FIG. 4 showing the catheter distal end just contacting the stone;

FIG. 5 shows the balloon portion of the catheter partly inflated due to pressure being applied to the balloon;

FIG. 6 shows the balloon inflated to distend the ureter to a greater diameter than the stone and the application of suction to hold the stone against the distal end of the catheter;

FIG. 7 shows the catheter with the balloon inflated and the catheter partially withdrawn permitting the stone to drop and the beginning of intussusception of the balloon; and FIG. 8 shows further withdrawal of the catheter with the stone being enveloped due to almost complete intussusception of the balloon.

DETAILED DESCRIPTION OF THE PREFERRED EMBODIMENT

Figure 4:
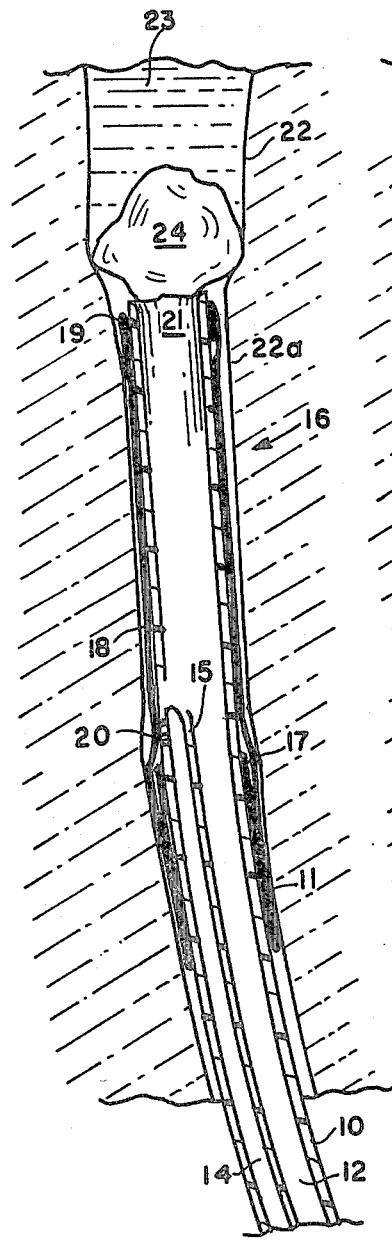

FIG. 1 illustrates the construction of the distal end of the intussuscepting catheter 10 of the invention shown in cross sectional view as well as a portion of the proximal end. The cylindrical catheter 10, which may be formed from a plastic which is flexible yet sufficiently stiff as to be inserted into passages in the human body; for example, through the ureter from the bladder to the kidney. Polyethylene is a suitable material, although there are other types of material which will be obvious to those of skill in the art. Catheter 10 includes a first lumen 12 which is open at the distal end, which end is slightly flared and rounded as shown at 21 and a small lumen 14 which is closed at the distal end and includes an orifice 20 in an external wall thereof. As best seen in FIG. 2 which is a cross sectional view 2—2 and a plain through orifice 20. A portion of the proximal end is also shown in FIG. 1 in which lumen 14 divides from the catheter to a separate tube 15A to be connected to a pressure source by a connector 36 as described more fully below. Similarly, lumen 12 separates into a separate tube 10A for connection by means of connector 38 to a suction source. A tubular balloon portion 16 is formed from a length of thin, highly flexible and elastic material such as latex rubber or synthetic rubber, forming a sleeve. The upper end of the tubular balloon 16 is formed by folding the end inward and attaching to the outer periphery of catheter 10 at which point the end is secured thereto by a suitable adhesive, cement or other method of fusing or bonding as indicted at 19. The lower end of tubular balloon 16 is formed in a reentrant shape 17 and attached to catheter 10 just below orifice 20.

As will familar to those of skill in the art, the diameter of catheter 10 may be on the order 2 to 3 mm. The balloon tubing 16 is selected to form a fit over the distal end of the catheter 10 so as to be relatively snug yet not be subjected to stretching. The length of the reentrant portion may be on the order of 10 to 20 mm or approximately equal to the distance from the point of attachment of the reentrant portion to the distal end of the balloon.

As may now be understood, tubular balloon 16, when attached around the periphery of the catheter 10 as shown at 19 and 17, forms a closed balloon which may be inflated by applying air, water or other liquid or gasous materials via lumen 14 and connector 36 into balloon 16 as indicated by arrow A. Thus, balloon 16 will inflate and its diameter will increase. The overall length of catheter 10 may be selected in accordance with the ximum distance the catheter is expected to traverse during use as will be familar to the urologist.

The distal end of the catheter 10 may include a material, such as a wire, in the plastic which will be opaque to x-rays, thereby permitting the physician to observe the position of the catheter tip by fluoroscope. Similarly, the source of pressure for inflating balloon 16 may include a suitable opaque medium to indicate the degree of inflation being obtained during use.

An alternate design for the distal end of the catheter 10 is shown in FIG. 3. The catheter wall 32 is recessed slightly over the area surrounded by balloon wall 18 and has the same diameter as the catheter tip 33. This permits tip 33 to be moved through a small ureter without interference to the balloon attachment 31. The portion of catheter 30 below balloon 18 preferably is the same diameter as tip 33.

Having shown the typical construction of a catheter in accordance with my invention, the manner in which the invention used will now be described. Assuming that a patient has been found to have a kidney stone obstructing the ureter adjacent the kidney pelvis. A catheter is selected having a diameter appropriate to the diameter of the patient's ureter. The catheter is passed through a cystoscope into the bladder, and then into the ureter. Preferably under fluoroscope, the catheter is inserted as indicated in FIG. 4 until the distal end 21 contacts the stone 24. In accordance with normal practice, lubricants may be used to ease insertion of the catheter 10. As will be noted from FIG. 4, urine 23 trapped above stone 24 will normally exert downward pressure tending to force stone 24 against the narrow ureter walls.

Figure 5:
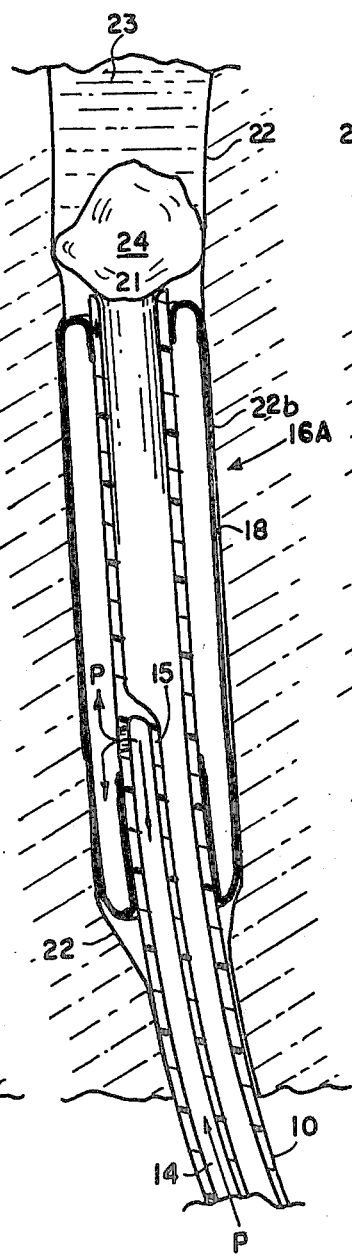
Figure 6:
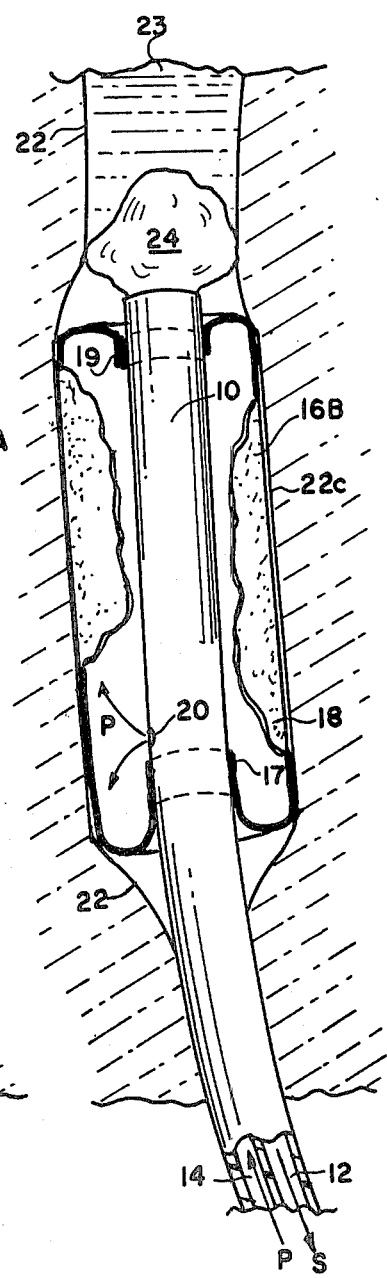

After insertion of catheter 10 into ureter 22 to the point indicated in FIG. 4, pressure is applied via lumen 14 into balloon 16. Thus, balloon 16 will expand as indicated in FIG. 5 at 16A, dilating the ureter walls 22b over the length of balloon 16A. If pressure is being applied by a liquid x-ray medium, the physician may note the amount of dilation being produced. Preferably, balloon 16 will be inflated to a degree, as indicated in FIG. 6 at 16B, that ureter 22 is slightly larger in diameter than stone 24. At this time, suction may be applied via lumen 12 and tube 10A which will tend to pull stone 24 into the flared distal end 21 of lumen 12. If stone 24 is relatively smooth, a seal between stone 24 and end 21 may occur at this point.

Figure 7:
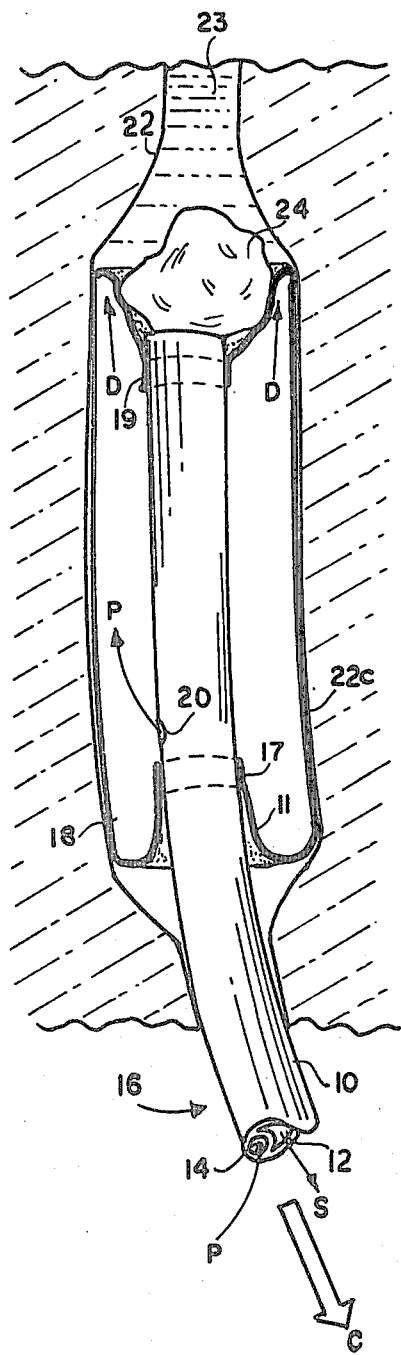

Next, as shown by arrow C in FIG. 7, catheter 10 is very slowly withdrawn. The pressure of urine 23 above the stone will assist in forcing the stone downward through the ureter into the enlarged or distended portion produced by balloon 16. Due to the flexibility of balloon 16, withdrawal of catheter 10 will result in the outer surface of the balloon, which is being held by pressure against the ureteral wall, to remain stationary and the distal end of balloon 16 will begin to intussusceptate as indicated by arrows D. Similarly, the reentrant portion 11 will begin roll outward and therefore shorten. Pressure P is maintained in balloon 16 during this phase by means of a cutoff valve to lumen 14A or by manipulating the source of pressure appropriately.

Figure 8:
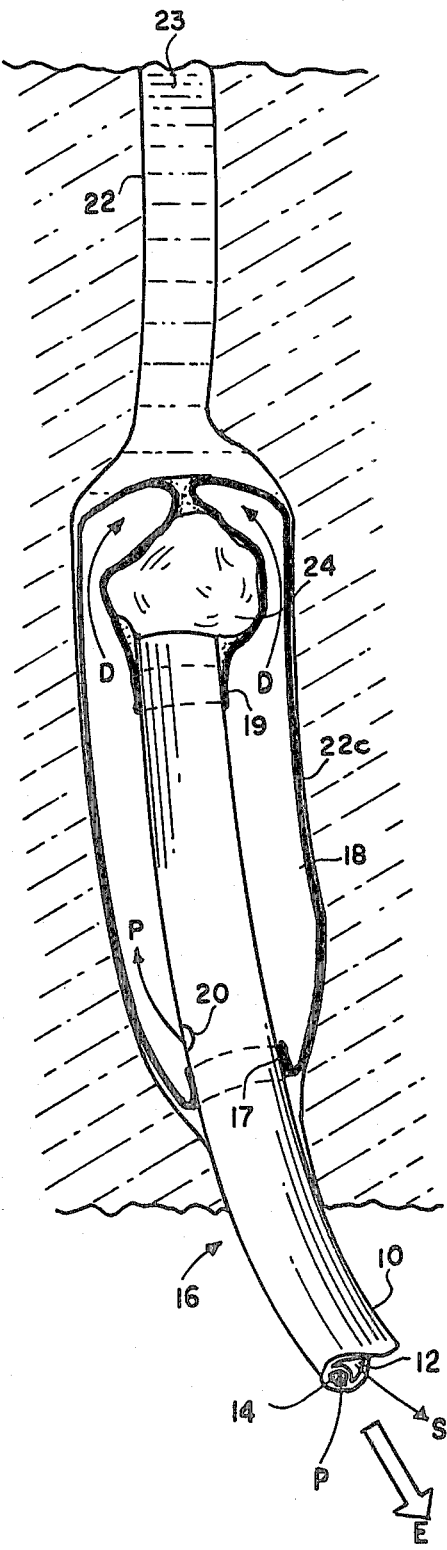

Turning to FIG. 8, the result of continuing withdrawal of catheter 10 is indicated in which balloon 16 has almost completely intussuscepted around stone 24. Suction is being maintained on lumen 12 and it will be understood that the very thin elastic material forming balloon 16 will tend conform to any irregularities in stone 24, essentially sealing the stone in the pocket formed by the intussusceptated portion of the balloon 16. Therefore, the suction S is effective in gripping stone 24 such that it will follow the withdrawal of the catheter. In addition, as stone 24 is totally enveloped as shown at 26, and pressure P is maintained, a pliable, flexible basket is seen to be formed. Thus, the pressure of urine 23 above stone 24, the suction from lumen 12, and the gripping of the stone 24 by balloon 16 cooperate to permit withdrawal of the catheter into the bladder for final removal of the stone.

Although the invention has been disclosed herein with application to extraction of ureteral stones from the upper end of the ureter, it will be clear to physicians that the novel balloon catheter is suitable for removal of foreign objects from other passages in the human body with minimum trauma or damage. The simple construction permits the device to be produced at low cost and to be disposable after one use.

The invention has been discribed with reference to a particular embodiment. However, it will be obvious to those of skill in the art to make modifications and variations in the exemplary embodiments without departing from the spirit and scope of the invention.

I claim:

1. A balloon catheter for extracting a ureteral stone from a ureter comprising:

an outer flexible cylindrical tube having an open distal end for insertion into a ureter and a connection thereto at the proximal end of said outer tube;

an inner flexible tube within and coextensive with said outer tube and having a common wall therewith, said inner tube closed at its distal end, having an orifice adjacent its distal end through said common wall, and having a connection thereto at the proximal end of said outer tube;

an elongate distensible elastic sleeve disposed concentrically with said outer tube having a distal end folded inward for a distance sufficient for attaching said sleeve distal end circumjacent to the distal end of said outer tube and a proximal end portion folded inward to thereby form an extended reentrant portion, the proximal end of said reentrant end portion attached circumjacent to said outer tube below said orifice;

means for selectively applying pressure to said connection of said inner tube after said outer tube is inserted into a ureter for inflating said elastic sleeve for dilating said ureter to a diameter greater than a stone in said ureter; and said elastic sleeve is adapted to have its outer wall frictionally engaged with the wall of said ureter when inflated to initially remain stationary upon withdrawal of said outer tube from said ureter, said distal end of said sleeve thereby unfolding and intussuscepting to capture and substantially enclose a stone whereby further withdrawal of said outer tube withdraws said inflated elastic sleeve for extraction of said stone from said ureter.

2. The catheter as defined in claim 1 in which said connection to said outer tube is connected to a source of suction for drawing a stone into contact with said open distal end of said outer tube.

3. The catheter as defined in claim 1 in which said pressure applying means includes means for injecting an x-ray opaque medium through said inner tube and said orifice for inflating said elastic sleeve.

4. The cathether as defined in claim 1 in which said elastic sleeve is made from thin latex rubber.

5. The device as defined in claim 1 in which said means for applying pressure includes means for injecting an x-ray opaque medium into said elastic tube for permitting observation thereof by fluoroscope.

6. A device for extracting stones or other foreign objects from passages in a human body comprising;
a flexible essentially cylindrical catheter having a distal end for insertion into a passage in a human body a sufficient distance to contact a foreign object in said passage, said catheter having a first lumen open at said distal end and a second lumen closed at said distal end, said second lumen having an orifice through the exterior wall of said catheter adjacent said distal end, said catheter having a proximal end maintained external to the human body;
an inflatable flexible elastic tube having an outer end folded inwardly sufficiently to be attached circumjacent to said distal end of said catheter, and having an inner end folded inwardly in reentrant fashion and attached circumjacent to said catheter below said orifice whereby said orifice provides communication between said second lumen and said elastic tube, the length of said folded inner end being much greater than the length of said folded outer end;
means for selectively applying pressure to said second lumen at the proximal end of said catheter for inflating said elastic tube via said orifice for dilating said passage to a diameter greater than that of said foreign object; and
said inflated elastic tube having its outer wall frictionally engaged with the wall of said passage upon inflation to remain initially essentially stationary upon slow withdrawal of said catheter from said passage, said upper folded end thereby unfolding and intussuscepting to capture and to substantially enclose said foreign body, and said lower folded end simultaneously unfolding, said withdrawal of said catheter thereafter moving said inflated elastic tubing and said enveloped foreign body along said passage for extraction therefrom.

7. The device as defined in claim 5 in which:
said first lumen includes a connection thereto disposed at said proximal end of said catheter; and
said first lumen connection is connected to a source of suction whereby said foreign object is drawn to said distal end of said catheter and said suction cooperates with said intussuscepted portion of said inflated elastic tube to envelope said foreign object for extraction.

8. A device for insertion into the ureter for contacting and extracting a stone from the ureter comprising:
an elongate inflatable sleeve having a distal end folded inward for a short distance and a proximal end folded inward for a distance longer than said folded distal end to thereby form a reentrant portion;
a double lumen catheter having said sleeve disposed circumjacent to said catheter, said folded distal end of said sleeve attached to said catheter at the catheter distal end and said proximal end of said sleeve attached to said catheter to form a snug fit of said sleeve along said catheter;
a first lumen of said double lumen catheter communicating with the interior of said inflatable sleeve to permit inflation thereof for applying an outward radial force to the walls of the ureter to thereby dilate said ureter to a diameter greater than that of said stone;
a second lumen of said double lumen catheter having an opening at said catheter distal end for contacting said stone and for applying suction thereto to maintain said stone in contact with said catheter distal end; and
said inflatable sleeve adapted to intussuscept after inflation as said catheter is withdrawn from said ureter to thereby captivate said stone permitting extraction of said captivated stone from said ureter without trauma to the ureteral walls.

9. The device as defined in claim 8 in which said catheter includes a circumferential recessed portion adjacent to said distal end thereof whereby said sleeve when in its uninflated condition lies within said recessed portion.

10. The device as defined in claim 9 in which said catheter includes a distal end having a connection to said second lumen for coupling to a source of suction, and said first lumen includes a connection for coupling to a source of pressure.

11. The device as defined in claim 10 in which said first lumen is connected to a source of air pressure.

12. The device as defined in claim 10 in which said lumen is attached to a source of fluid under pressure.

13. The device as defined in claim 12 in which said fluid is opaque to x-rays.

* * * * *